United States Patent
Matta et al.

(10) Patent No.: US 12,137,961 B2
(45) Date of Patent: Nov. 12, 2024

(54) ELECTROSURGICAL PENCIL WITH A PROTECTIVE GUARD

(71) Applicant: Covidien LP, Mansfield, MA (US)

(72) Inventors: George S. Matta, Plainville, MA (US); Jacob C. Baril, Norwalk, CT (US); Matthew A. Dinino, Newington, CT (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 687 days.

(21) Appl. No.: 16/814,123

(22) Filed: Mar. 10, 2020

(65) Prior Publication Data

US 2020/0305954 A1    Oct. 1, 2020

Related U.S. Application Data

(60) Provisional application No. 62/823,240, filed on Mar. 25, 2019.

(51) Int. Cl.
*A61B 18/14*   (2006.01)
*A61B 18/00*   (2006.01)
*A61B 18/16*   (2006.01)

(52) U.S. Cl.
CPC .............. *A61B 18/14* (2013.01); *A61B 18/16* (2013.01); *A61B 2018/00589* (2013.01); *A61B 2018/00601* (2013.01); *A61B 2018/1412* (2013.01)

(58) Field of Classification Search
CPC .......... A61B 18/16; A61B 2018/00589; A61B 2018/00601; A61B 2018/1412
See application file for complete search history.

(56) References Cited

U.S. PATENT DOCUMENTS

| | | |
|---|---|---|
| 2,022,065 A | 11/1935 | Wappler |
| 2,047,535 A | 7/1936 | Wappler |
| 3,516,412 A | 6/1970 | Ackerman |
| 3,886,944 A | 6/1975 | Jamshidi |
| 4,161,950 A | 7/1979 | Doss et al. |
| 4,196,734 A | 4/1980 | Harris |
| 4,198,957 A | 4/1980 | Cage et al. |
| 4,485,810 A | 12/1984 | Beard |
| 4,534,347 A | 8/1985 | Taylor |
| 4,622,966 A | 11/1986 | Beard |
| 4,633,880 A | 1/1987 | Osypka et al. |

(Continued)

*Primary Examiner* — Joseph A Stoklosa
*Assistant Examiner* — Annie L Shoulders
(74) *Attorney, Agent, or Firm* — Carter, DeLuca & Farrell LLP

(57) ABSTRACT

An electrosurgical pencil includes a body. The body includes a track extending along a distal end of the body. A treatment blade extends from the distal end of the body and is electrically connected to a first potential of a source of electrosurgical energy. The treatment blade is configured to treat tissue upon activation thereof. A protective guard is configured to slide along a track between a first position concealing a distal end of the treatment blade and a second position exposing the distal end of the treatment blade. A return electrode is disposed on an exposed surface of the protective guard. The return electrode is electrically connected to a second potential of the source of electrosurgical energy. A biasing member includes a first end operably connected to the distal end of the body and a second end operably connected to the protective guard.

20 Claims, 3 Drawing Sheets

(56) References Cited

U.S. PATENT DOCUMENTS

| | | | |
|---|---|---|---|
| 4,862,890 A | 9/1989 | Stasz et al. | |
| 5,013,312 A | 5/1991 | Parins et al. | |
| 5,071,426 A * | 12/1991 | Dolgin | A61B 17/3211 |
| | | | 30/151 |
| 5,085,659 A | 2/1992 | Rydell | |
| 5,300,068 A | 4/1994 | Rosar et al. | |
| 5,360,428 A | 11/1994 | Hutchinson, Jr. | |
| 5,423,760 A | 6/1995 | Yoon | |
| 5,441,499 A | 8/1995 | Fritzsch | |
| 5,531,744 A | 7/1996 | Nardella et al. | |
| 5,536,267 A | 7/1996 | Edwards et al. | |
| 5,599,295 A | 2/1997 | Rosen et al. | |
| 5,599,346 A | 2/1997 | Edwards et al. | |
| 5,611,798 A | 3/1997 | Eggers | |
| 5,647,871 A * | 7/1997 | Levine | A61B 18/1442 |
| | | | 606/49 |
| 6,027,501 A | 2/2000 | Goble et al. | |
| 6,217,528 B1 | 4/2001 | Koblish et al. | |
| 6,458,125 B1 | 10/2002 | Cosmescu | |
| 6,494,881 B1 | 12/2002 | Bales et al. | |
| 6,530,924 B1 | 3/2003 | Ellman et al. | |
| 6,533,781 B2 | 3/2003 | Heim et al. | |
| 6,752,767 B2 | 6/2004 | Turovskiy et al. | |
| 7,033,354 B2 | 4/2006 | Keppel | |
| 7,371,234 B2 | 5/2008 | Young | |
| 7,399,299 B2 | 7/2008 | Daniel et al. | |
| 7,419,488 B2 | 9/2008 | Ciarrocca et al. | |
| 7,500,974 B2 | 3/2009 | Sartor | |
| 7,846,108 B2 | 12/2010 | Turovskiy et al. | |
| 7,846,158 B2 | 12/2010 | Podhajsky | |
| 8,137,345 B2 | 3/2012 | McNall, III et al. | |
| 8,875,405 B2 | 11/2014 | Trees et al. | |
| 8,968,301 B2 | 3/2015 | Weber | |
| 9,060,765 B2 | 6/2015 | Rencher et al. | |
| 9,358,065 B2 | 6/2016 | Ladtkow et al. | |
| 9,445,863 B2 | 9/2016 | Batchelor et al. | |
| 9,775,665 B2 | 10/2017 | Ellman | |
| 9,993,287 B2 | 6/2018 | Sartor et al. | |
| 10,045,761 B2 | 8/2018 | Weber | |
| 10,342,607 B1 * | 7/2019 | Reaux | A61B 18/1206 |
| 10,376,314 B2 | 8/2019 | van der Weide et al. | |
| 10,433,898 B2 | 10/2019 | Borgmeier et al. | |
| 10,433,899 B2 | 10/2019 | Borgmeier et al. | |
| 10,531,917 B2 | 1/2020 | Johnson et al. | |
| 2005/0070895 A1 | 3/2005 | Ryan et al. | |
| 2005/0283149 A1 | 12/2005 | Thorne et al. | |
| 2006/0293655 A1 * | 12/2006 | Sartor | A61B 18/1402 |
| | | | 606/49 |
| 2007/0078454 A1 | 4/2007 | McPherson | |
| 2007/0118110 A1 | 5/2007 | Girard et al. | |
| 2007/0149966 A1 | 6/2007 | Dahla et al. | |
| 2007/0179494 A1 | 8/2007 | Faure | |
| 2007/0219546 A1 | 9/2007 | Mody et al. | |
| 2007/0260240 A1 | 11/2007 | Rusin | |
| 2007/0265609 A1 | 11/2007 | Thapliyal et al. | |
| 2008/0281323 A1 | 11/2008 | Burbank et al. | |
| 2009/0306642 A1 | 12/2009 | Vankov | |
| 2012/0330307 A1 | 12/2012 | Ladtkow et al. | |
| 2013/0331830 A1 * | 12/2013 | Podhajsky | A61B 18/1445 |
| | | | 606/29 |
| 2016/0074061 A1 * | 3/2016 | Neurohr | A61B 17/320092 |
| | | | 606/169 |
| 2017/0042609 A1 * | 2/2017 | Gittard | A61B 18/16 |
| 2018/0206903 A1 * | 7/2018 | Podany | A61B 18/1442 |
| 2019/0083172 A1 | 3/2019 | Ladtkow et al. | |

* cited by examiner

ELECTROSURGICAL PENCIL WITH A PROTECTIVE GUARD

CROSS-REFERENCE TO RELATED APPLICATIONS

The present application claims the benefit of and priority to U.S. Provisional Patent Application No. 62/823,240, filed on Mar. 25, 2019. The entire contents of all of the foregoing applications are incorporated by reference herein.

BACKGROUND

Technical Field

The present disclosure relates to an electrosurgical instrument, and more particularly, to an electrosurgical pencil with a protective guard.

The coagulation of blood vessels is a necessary part of medical surgery and can be performed by an electrosurgical instrument commonly known as an electrosurgical pencil or coagulator pencil. With this type of pencil, an electrically conductive metal tip (e.g., in the form of a blade or a needle) extends outwardly from the distal end of the body of the pencil, the latter acting as a hand grip for a surgeon using the pencil. In use, the tissue of a patient is typically electrically connected to one side of an electrosurgical circuit via a return pad, and the electrically conductive tip is typically connected to the other side of the same circuit. When the metal tip touches or is near the tissue at the surgical site, a high frequency electrical current flows from the electrode to the tissue, thus coagulating and cauterizing the tissue.

Typical electrosurgical pencils allow the surgeon to change between two pre-configured settings (e.g., coagulation and cutting) via two discrete buttons disposed on the electrosurgical pencil itself. Other electrosurgical pencils allow the surgeon to increment the power applied when the coagulating or cutting activation button of the instrument is actuated by adjusting or closing a switch on the electrosurgical generator utilizing a potentiometer circuit. Still other electrosurgical pencils offer a third button which provides a so-called "blend" waveform or algorithm generally between the cutting waveform and the coagulation waveform.

SUMMARY

An electrosurgical pencil provided in accordance with aspects of the present disclosure includes a body including a proximal end and a distal end. The body includes a track extending along the distal end of the body. A treatment blade extends from the distal end of the body and is electrically connected to a first potential of a source of electrosurgical energy. The treatment blade is configured to treat tissue upon activation thereof. A protective guard is slidably coupled to the distal end of the body and is operably engaged with the track. The protective guard is configured to slide along the track between a first position concealing a distal end of the treatment blade and a second position exposing the distal end of the treatment blade. A return electrode is disposed on an exposed surface of the protective guard. The return electrode is electrically connected to a second potential of the source of electrosurgical energy. A biasing member includes a first end operably connected to the distal end of the body and a second end operably connected to the protective guard. The biasing member is configured to bias the protective guard in the first position concealing the distal end of the treatment blade.

The protective guard is configured to expose the treatment blade when the protective guard is forced against tissue. A distal end of the protective guard is distally positioned with respect to the distal end of the treatment blade when the protective guard is in the first position concealing the distal end of the treatment blade.

In aspects according to the present disclosure, at least a portion of the return electrode is configured to contact tissue when pressure is applied to the protective guard to move the protective guard from the first position concealing the distal end of the treatment blade to the second position exposing the distal end of the treatment blade. At least a portion of the return electrode extends along an outside of the protective guard. At least a portion of the return electrode extends along an outside of at least a portion of the body.

In aspects according to the present disclosure, the biasing member is a spring. The spring is positioned about the treatment blade. The spring positioned about the treatment blade is spaced from the treatment blade to prevent contact therewith.

In aspects according to the present disclosure, the treatment blade includes a mechanical profile to facilitate cutting.

In aspects according to the present disclosure, the treatment blade is electrically connected to a switch operably disposed on the body. The switch is activatable to supply electrosurgical energy to the treatment blade using an energy algorithm. The energy algorithm includes at least one of a cutting algorithm, a coagulating algorithm or a blending algorithm.

In aspects according to the present disclosure, the protective guard includes an opening defined therein configured to pass the distal end of the treatment blade therethrough.

An electrosurgical pencil provided in accordance with another aspect of the present disclosure includes a body including a proximal end and a distal end. The body includes a track extending along the distal end of the body. A treatment blade extends from the distal end of the body and is electrically connected to a first potential of a source of electrosurgical energy. The treatment blade is configured to treat tissue upon activation thereof. A protective guard is operably engaged with the track. The protective guard is configured to slide along the track between a first position concealing a distal end of the treatment blade and a second position exposing the distal end of the treatment blade. A return electrode is disposed on a surface of the protective guard. The return electrode is electrically connected to a second potential of the source of electrosurgical energy. A biasing member includes a first end operably connected to the distal end of the body and a second end operably connected to the protective guard. The biasing member is configured to bias the protective guard in the first position concealing the distal end of the treatment blade.

BRIEF DESCRIPTION OF THE DRAWINGS

The accompanying drawings, which are incorporated in and constitute a part of this specification, illustrate embodiments of the present disclosure and, together with the detailed description below, serve to further explain the present disclosure, in which.

DETAILED DESCRIPTION

Figure 1:
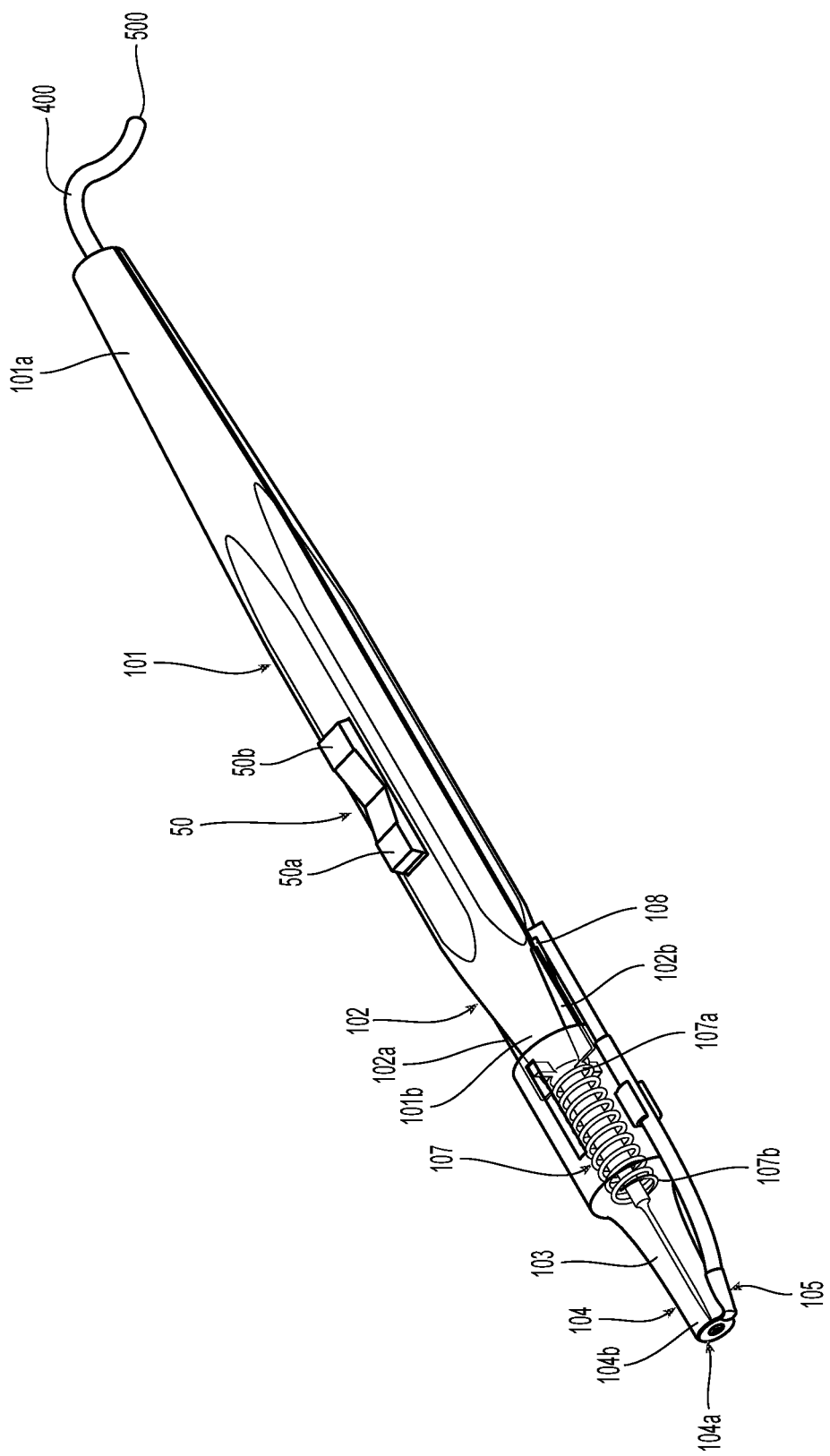
FIG. 1 is a perspective view of an electrosurgical pencil including a protective guard according to an exemplary embodiment of the present disclosure.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

"About" or "approximately" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

Descriptions of technical features or aspects of an exemplary embodiment of the present disclosure should typically be considered as available and applicable to other similar features or aspects in another exemplary embodiment of the present disclosure. Accordingly, technical features described herein according to one exemplary embodiment of the present disclosure may be applicable to other exemplary embodiments of the present disclosure, and thus duplicative descriptions may be omitted herein.

Exemplary embodiments of the present disclosure will be described more fully below (e.g., with reference to the accompanying drawings). Like reference numerals may refer to like elements throughout the specification and drawings. The terms "electrostatic pencil" and "electrostatic pen" may be used interchangeably herein.

Turning initially to FIG. 1, an electrosurgical pencil 10 including a protective guard 104 is shown according to an exemplary embodiment of the present disclosure.

Electrosurgical pencil 10 includes a body 101 having a proximal end 101a and a distal end 101b. The body 101 includes a track 102 extending along the distal end 101b of the body 101. A treatment blade 103 extends from the distal end 101b of the body 101. The treatment blade 103 is electrically connected to a first potential of a source of electrosurgical energy, e.g., generator 500, and is configured to treat tissue upon activation thereof.

Figure 2A:
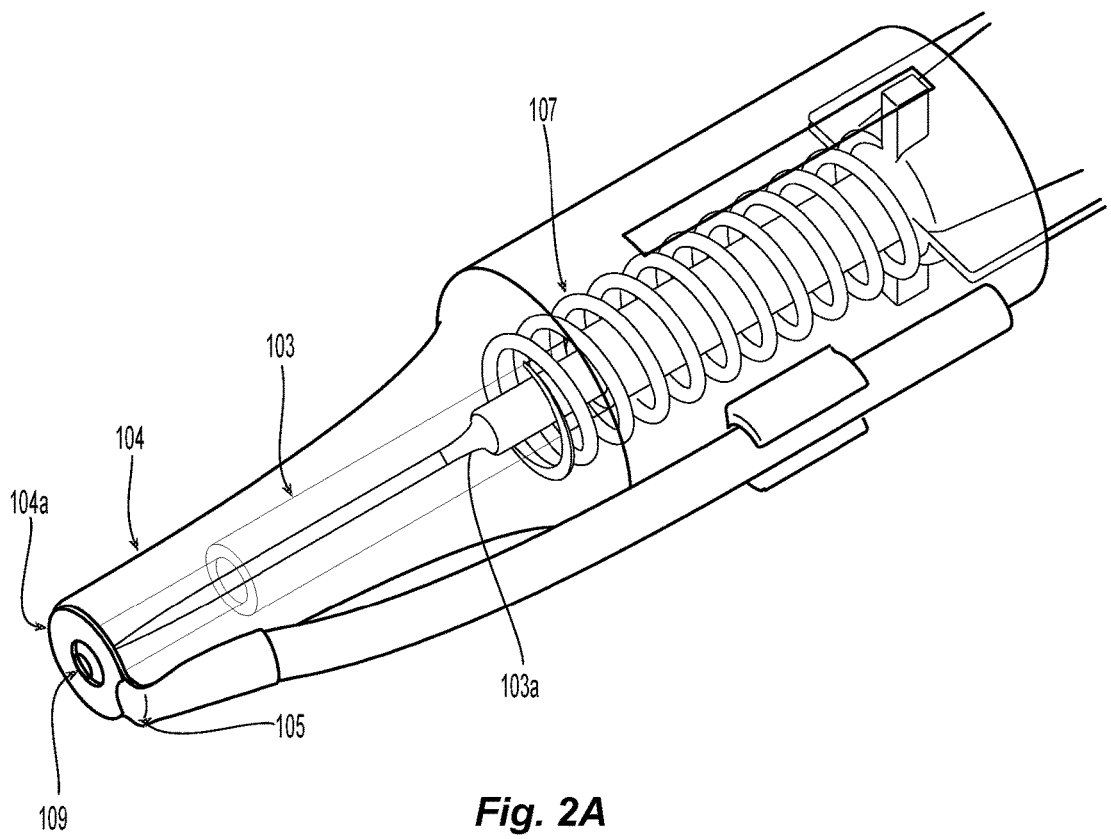
FIG. 2A is an enlarged perspective view of the electrosurgical pencil of FIG. 1 with the protective guard concealing a distal end of a treatment blade.
Figure 2B:
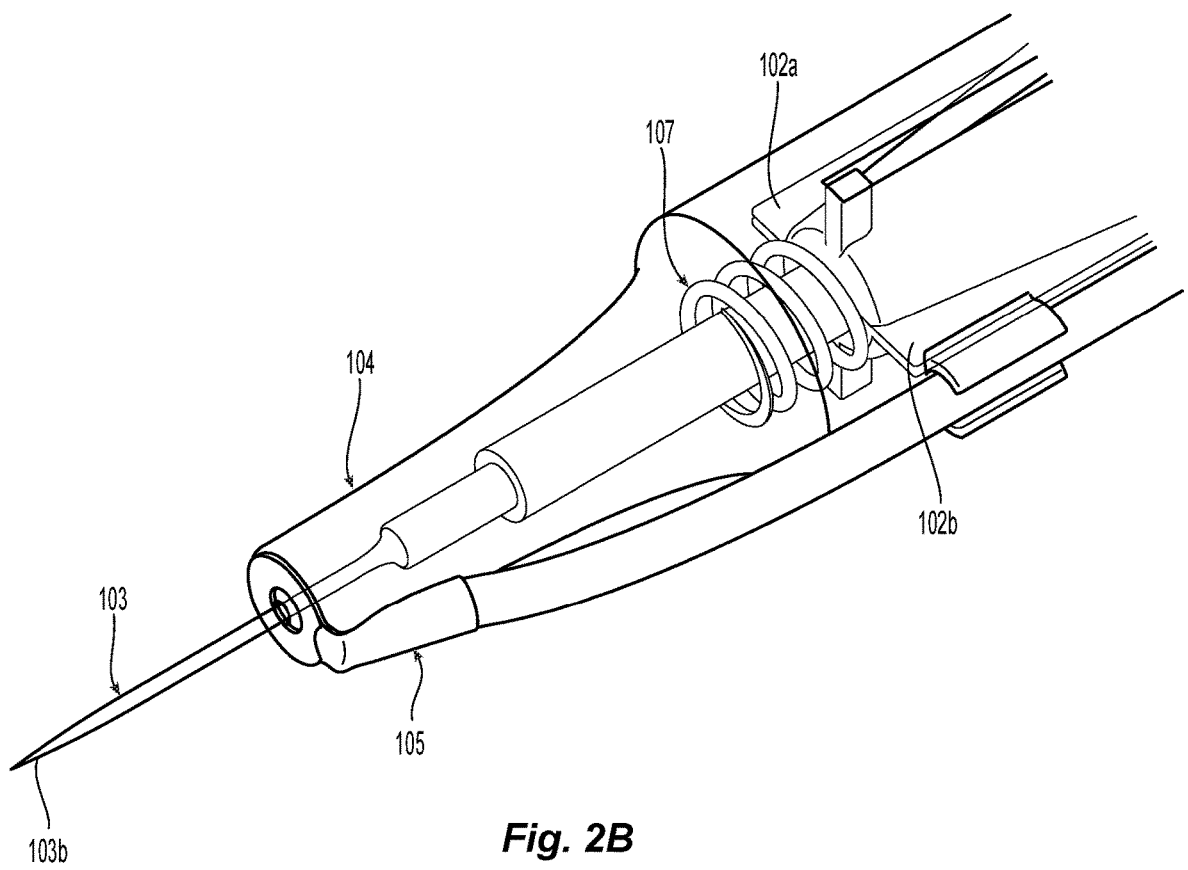
FIG. 2B is an enlarged perspective view of the electrosurgical pencil of FIG. 1 with the protective guard exposing a distal end of a treatment blade.

The protective guard 104 is slidably coupled to the distal end 101b of the body and is operably engaged with the track 102. Protective guard 104 is configured to slide along the track 102 between a first position concealing the distal end 103b of the treatment blade 103 (see, e.g., FIG. 2A) and a second position exposing the distal end 103b of the treatment blade 103 (see, e.g., FIG. 2B). The track 102 may include a first track 102a and a second track 102b. The first and second tracks 102a and 102b may be positioned at opposite sides of the distal end 101b of the body 101.

The protective guard 104 includes an opening 109 defined therein configured to pass the distal end 103b of the treatment blade 103 therethrough. The opening 109 faces away from the body 101.

A return electrode 105 is disposed on an exposed surface 104a of the protective guard 104 and is electrically connected to a second potential of the source of electrosurgical energy, e.g., generator 500. A biasing member 107 is operably coupled to the protective guard 104 and includes a first end 107a operably connected to the distal end 101b of the body 101 and a second end 107b operably connected to the protective guard 104. The biasing member 107 is configured to bias the protective guard 104 in the first position (see, e.g., FIG. 2A) concealing the distal end 103b of the treatment blade 103.

The exposed surface 104a of the protective guard 104 may face away from the body 101 and thus may be positioned to directly contact tissue. Thus, contact between the return electrode 104 and the contacted tissue may be constantly maintained.

The protective guard 104 is configured to expose the treatment blade 103 through opening 109 when the protective guard 104 is forced against tissue. A distal end 104b of the protective guard 104 is distally positioned with respect to the distal end 103b of the treatment blade 103 when the protective guard 104 is in the first position concealing the distal end 103b of the treatment blade 103. Thus, the distal end 103b of the treatment blade 103 is recessed inside the opening 109 to protect the treatment blade 103 and to prevent undesired contact with the treatment blade 103 (e.g., by adjacent tissue), such as when the treatment blade 103 is in the second position (see, e.g., FIG. 2B).

At least a portion of the return electrode 105 (e.g., the portion of the return electrode 105 disposed on the exposed surface 104a of the protective guard 104) is configured to contact tissue when pressure is applied to the protective guard 104 to move the protective guard 104 from the first position concealing the distal end 103b of the treatment blade 103 to the second position exposing the distal end 103b of the treatment blade 103. At least a portion of the return electrode 105 may be configured to extend along an outside of the protective guard 104. At least a portion of the return electrode 105 may be configured to extend along an outside of the body 101. The return electrode 105 may be attached to a portion of the protective guard 104 such that the return electrode slides with the protective guard 104 along the track 102.

The biasing member 107 may be a spring (e.g., a compression spring, such as the compression spring 301 described in more detail below with reference to FIG. 3). The biasing member 107 may be positioned about the treatment blade 103 or may be spaced from the treatment blade 103 to prevent contact therewith.

The treatment blade 103 may include a mechanical profile to facilitate cutting. For example, the treatment blade 103 may have a sharp tip formed at the distal end 103b thereof.

The treatment blade 103 is electrically connected to a switch 50 operably disposed on the body 101. The switch 50 is activatable to supply electrosurgical energy to the treatment blade 103 using an energy algorithm. The energy algorithm includes a cutting algorithm, a coagulating algorithm and/or a blending algorithm. The switch 50 is described in more detail below.

As mentioned above, treatment blade 103 extends from the distal end 101b of body 101 and is configured to connect to electrosurgical energy source 500 via one or more leads extending through body 101 and through a cable 400 extending from proximal end 101a of body 101. Treatment blade 103 may be configured to electrically cut tissue but may also include a mechanical edge (e.g., a sharp tip) to facilitate same. Treatment blade 103 may include an insulator 103a disposed at a proximal end thereof configured to insulate the body 101 and other parts of the electrosurgical pencil 10 from stray electrical currents during activation.

As mentioned above, pencil 10 also includes a switch, e.g., toggle switch 50, that includes distal and proximal ends 50a and 50b. Any type of switch 50 or switches may be employed depending on a particular surgical purpose of a particular surgical need. As shown, toggle switch 50 is configured to electrically communicate with the electrosurgical energy source 500 (e.g., a generator) to selectively supply energy to the treatment blade 103. When toggled in the distal direction, e.g., toward distal end 50a, an electrical cutting algorithm is generated by the electrosurgical energy source 500. When toggled in the proximal direction, e.g., toward proximal end 50b, an electrical coagulating algorithm is generated by the electrosurgical energy source 500. Other electrical algorithms may be utilized with other switch types or multiple switch arrangements. For example, U.S. Pat. Nos. 7,244,257, 7,156,842 detail various such switch arrangements for use with electrosurgical pencils, the entire contents of each of which being incorporated by reference herein.

The treatment blade 103 may include a non-stick coating to reduce tissue adhesion, thus preventing undesired damage to tissue. As an example, the outer surface of the treatment blade 103 may include a nickel-based material. The treatment blade 103 may be formed by coating a base layer, stamping a desired shape, or metal injection molding. The non-stick coating is designed to reduce adhesion between the treatment blade 103 (and/or components thereof) with the surrounding tissue during activation and cutting. As an example, the non-stick coating may include nickel-chrome, chromium nitride, MedCoat 2000 manufactured by The Electrolizing Corporation of OHIO, inconel 600 or tin-nickel. Other tissue contacting surfaces, e.g., return electrode 105 may also be coated with one or more of the above materials to achieve the same result, i.e., a "non-stick surface." These non-stick materials are of a class of materials that provide a smooth surface to prevent mechanical tooth adhesions. Reducing the amount that the tissue "sticks" during treatment improves the overall efficacy of the electrosurgical pencil 10 described herein.

Figure 3:
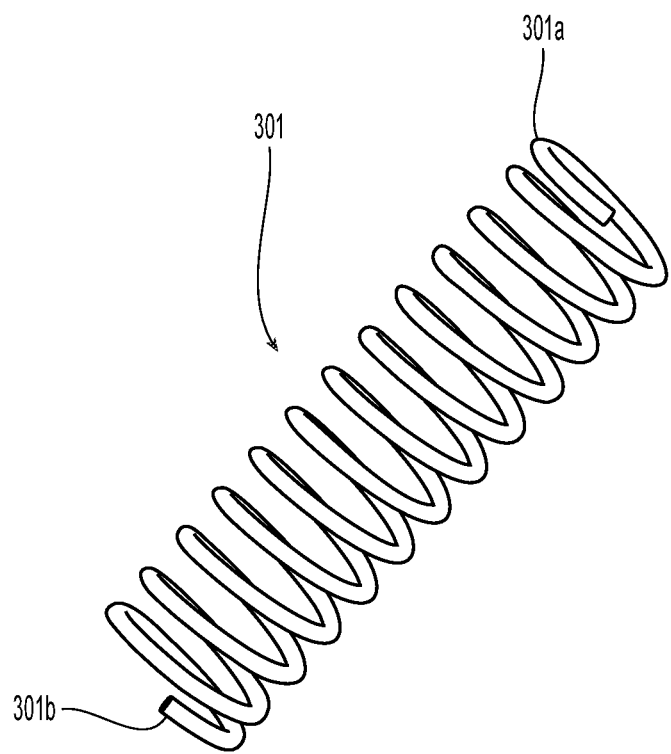
FIG. 3 is an enlarged view of an exemplary biasing member according to an exemplary embodiment of the present disclosure.

Referring to FIG. 3, the biasing member 107 may be a spring 301 (e.g., a compression spring). Spring 301 may be positioned about the treatment blade 103 or may be spaced from the treatment blade 103 to prevent contact therewith. The spring 301 may include a first end 301a and a second end 301b opposite the first end 301a. The first end 301a of the spring 301 may be attached to the distal end 101b of body 101. The second end 301b of the spring 301 may be attached to the protective guard 104. Thus, the spring 301 may be used to bias the protective guard 104 into the first position (see, e.g., FIG. 2A).

During use, a surgeon may orient the electrosurgical pencil 10 to treat tissue (e.g., coagulate, blend, cut) and push the protective guard 104 against the tissue. The exposed surface 104a including opening 109 of the protective guard 104 forces the protective guard 104 to expose the treatment blade 103, e.g., cutting blade, by passing the treatment blade 103 through opening 109 and into tissue. Energy is then applied by toggling switch 50 in the desired direction to treat tissue. Once tissue treatment is completed, the toggle switch 50 may be activated again to apply a different energy modality or the surgeon can simply disengage the tissue to automatically return (via the bias of spring 301) the protective guard 104 to the closed position about the treatment blade 103.

The protective guard 104 may be configured as an accessory component configured to be connected to a body of traditional electrosurgical pencil, e.g., added to a pre-existing electrosurgical pencil as an add-on component. Alternatively, the protective guard 104 may be an integrally formed feature of electrosurgical pencil 10.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical pencil, comprising:
a body including a proximal end and a distal end, the body including a track extending along the distal end of the body;
a treatment blade extending from the distal end of the body and electrically connected to a first potential of a source of electrosurgical energy;
a protective guard slidably coupled to the distal end of the body and operably engaged with the track, the protective guard configured to slide relative to the body along the track between a first position concealing a distal end of the treatment blade and a second position exposing the distal end of the treatment blade, wherein the protective guard in the first position surrounds the treatment blade;
a return electrode disposed on an exposed distal-facing surface of the protective guard such that the return electrode extends distally from a distal-most end of the protective guard, and contacting the exposed distal-facing surface to tissue is configured to bring the return electrode into contact with the tissue, wherein pressure applied on the tissue by the exposed distal-facing surface causes the protective guard to slide along the track from the first position toward the second position to expose the distal end of the treatment blade while the exposed distal-facing surface and the return electrode maintain contact with the tissue, the return electrode electrically connected to a second potential of the source of electrosurgical energy; and
a biasing member including a first end operably connected to the distal end of the body and a second end operably connected to the protective guard, the biasing member configured to bias the protective guard in the first position concealing the distal end of the treatment blade.

2. The electrosurgical pencil of claim 1, wherein the exposed distal-facing surface of the protective guard is distally positioned with respect to the distal end of the treatment blade when the protective guard is in the first position concealing the distal end of the treatment blade.

3. The electrosurgical pencil of claim 1, wherein at least a portion of the return electrode extends along an outside of the protective guard.

4. The electrosurgical pencil of claim 3, wherein at least a portion of the return electrode extends along an outside of at least a portion of the body.

5. The electrosurgical pencil of claim 1, wherein the biasing member is a spring.

6. The electrosurgical pencil of claim 5, wherein the spring is positioned about the treatment blade.

7. The electrosurgical pencil of claim 6, wherein the spring positioned about the treatment blade is spaced from the treatment blade to prevent contact between the treatment blade and the spring.

8. The electrosurgical pencil of claim 1, wherein the treatment blade includes a mechanical profile to facilitate cutting.

9. The electrosurgical pencil of claim 1, wherein the treatment blade is electrically connected to a switch operably disposed on the body, the switch activatable to supply electrosurgical energy to the treatment blade using an energy algorithm.

10. The electrosurgical pencil of claim 9, wherein the energy algorithm includes at least one of a cutting algorithm, a coagulating algorithm or a blending algorithm.

11. The electrosurgical pencil of claim 1, wherein the protective guard includes an opening defined through the exposed distal-facing surface and configured to receive the distal end of the treatment blade.

12. The electrosurgical pencil of claim 1, wherein the exposed distal-facing surface of the protective guard is distal-facing when the protective guard is in the first position.

13. The electrosurgical pencil of claim 1, wherein the protective guard in the second position surrounds a portion of the treatment blade.

14. An electrosurgical pencil, comprising:
a body including a proximal end and a distal end, the body including a track extending along the distal end of the body;
a treatment blade extending from the distal end of the body and electrically connected to a first potential of a source of electrosurgical energy;
a protective guard operably engaged with the track, the protective guard configured to slide relative to the body along the track between a first position concealing a distal end of the treatment blade and a second position exposing the distal end of the treatment blade, wherein the protective guard in the first position surrounds the treatment blade;
a return electrode disposed on a distal-facing surface of the protective guard such that the return electrode extends distally from a distal-most end of the protective guard, and contacting the distal-facing surface to tissue is configured to bring the return electrode into contact with the tissue, wherein pressure applied on the tissue by the distal-facing surface causes the protective guard to slide along the track from the first position toward the second position to expose the distal end of the treatment blade while the distal-facing surface and the return electrode maintain contact with the tissue, the return electrode electrically connected to a second potential of the source of electrosurgical energy; and
a biasing member including a first end operably connected to the distal end of the body and a second end operably connected to the protective guard, the biasing member configured to bias the protective guard in the first position concealing the distal end of the treatment blade.

15. The electrosurgical pencil of claim 14, wherein the distal-facing surface of the protective guard is distally positioned with respect to the distal end of the treatment blade when the protective guard is in the first position concealing the distal end of the treatment blade.

16. The electrosurgical pencil of claim 14, wherein the biasing member is a spring positioned about the treatment blade.

17. The electrosurgical pencil of claim 16, wherein the spring positioned about the treatment blade is spaced from the treatment blade to prevent contact between the treatment blade and the spring.

18. The electrosurgical pencil of claim 16, wherein the treatment blade includes a mechanical profile to facilitate cutting.

19. The electrosurgical pencil of claim 14, wherein the distal-facing surface of the protective guard is distal-facing when the protective guard is in the first position.

20. The electrosurgical pencil of claim 14, wherein the protective guard in the second position surrounds a portion of the treatment blade.

\* \* \* \* \*